United States Patent
Chern

(10) Patent No.: US 7,220,729 B2
(45) Date of Patent: *May 22, 2007

(54) HUNTINGTON'S DISEASE TREATMENT

(75) Inventor: Yijuang Chern, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 10/843,209

(22) Filed: May 10, 2004

(65) Prior Publication Data

US 2005/0250673 A1   Nov. 10, 2005

(51) Int. Cl.
*A61K 31/52* (2006.01)
*G01N 33/50* (2006.01)

(52) U.S. Cl. .................................... 514/46; 435/7.1

(58) Field of Classification Search ............... 514/45, 514/46

See application file for complete search history.

(56) References Cited

U.S. PATENT DOCUMENTS 4,968,697 A * 11/1990 Hutchison ..................... 514/46
5,714,460 A *  2/1998 Gluckman et al. ............. 514/3
6,124,125 A     9/2000 Kemp et al.
2004/0229837 A1* 11/2004 Chern et al.

OTHER PUBLICATIONS

Gamble J, Lopaschuk GD. 1997. Insulin inhibition of 5' adenosine . . . Metabolism 46(11):1270-1274.*
Moore, F. et al. 1991. Evidence that AMP triggers . . . Eur J Biochem 199:691-697.*
Bonelli, RM and Hofmann, P. 2004. A review of the treatment options for Huntington's disease. Exert Opin. Pharacother. 5(4):767-776.*
Popoli, P, Pezzola, A, Reggio, R, Caporali, MG, and de Carolis, AS. 1994. CGS21680 anatagonizes motor activity . . . European Journal of Pharmacology 257:R5-R6.*
Chern, Y. and Lee, Y-C. 2004. Application of CGS21680 and other agonists . . . http://www.sinica.edu.tw/~ip/Technology_e/12_MedBio/12A-911101_e.htm. Last updated Apr. 26, 2004.*
Hawley, SA et al. 5'-AMP activates the AMP-activated protein kinase cascade . . . 1995. J Biol Chem 45:27168-27191.*
Davies, SP et al. 1990. Location and function of three sites . . . Eur J Biochem 187:183-190.*
Chen, Z-P et al. 1999. AMP-activated protein kinase phosphorylation of endothelial NO synthase. FEBS letters 443:285-289.*
Jarvis et al. 1989. [3H]CGS21680, a selective A2 adenosine receptor agonist directly labels A2 receptors in rate brain. J Pharm Exp Therap 251(3):888-893.*
Suh YH et al. 2002. Pharmacological Reviews 54:469-525.*
Shaw RJ et al. 2004. PNAS 101:3329-3335.*
Sigma Catalog 2000-2001. p. 229.*
Sigma Catalog 1994. p. 582.*
Gamble, J. et al. 1997. Metabolism 46:1270-1274.*
Feigin et al. 2002. Curr Opin Neurol 15:483-489.*
Senatorov et al. 2004. Mol Psychiatry 9:371-385.*
Mazumder et al., 2003. Trends in Biochemical Sciences 28:91-98.*
Hsiao-Chun Cheng et al. "Essential Role of cAMP-response Element-binding Protein Activation by $A_{2A}$ Adenosine Receptors in Rescuing the Nerve Growth Factor-induced Neurite Outgrowth Impaired by Blockage of the MAPK Cascade". Journal of Biological Chemistry 277(37):33930-33942, 2002.
Wenzhen Duan et al. "Dietary restriction normalizes glucose metabolism and BDNF levels, slows disease progression, and increases survival in huntingtin mutant mice", PNAS 100(5):2911-2916, Mar. 4, 2003.
Robert J. Ferrante et al. "Neuroprotective Effects of Creatine in a Transgenic Mouse Model of Huntington's Disease". Journal of Neuroscience 20(12):4389-4397, Jun. 15, 2000.
Mari Garseth et al. "Proton Magnetic Resonance Spectorscopy of Cerebrospinal Fluid in Neurodegenerative Disease: Indication of Glial Energy Impairment in Huntington Chorea, but Not Parkinson Disease". Journal of Neuroscience Research 60:779-782, 2000.
Nai-Kuei Huang et al. "Activation of Protein Kinase A and Atopical Protein Kinase C and $A_{2A}$ Deprivation in PC12 Cells". Journal of Biological Chemistry 276(17):13838-13846, 2001.
Marc S. Hurlbert et al. "Mice Transgenic for an Expanded CAG Repeat in the Huntington's Disease Gene Develop Diabetes". Diabetes 48:649-651, Mar. 1999.
Bruce G. Jenkins et al. "Nonlinear Decrease over Time in N-Acetyl Aspartate Levels in the Absence of Neuronal Loss and Increases in Glutamine and Glucose in Transgenic Huntington's Disease Mice". Journal of Neurochemistry 74:2108-2119, 2000.
Guy A. Rutter et al. "Role of 5'-AMP-activated protein kinase (AMPK) in mammalian glucose homoeostatis". Journal of Biochemistry 375:1-16, 2003.
W. W. Winder. "Energy-sensing and signaling by AMP-activated protein kinase in skeletal muscle". J. Appl. Physiol. 91:1017-1028, 2001.
Gabriela da Silva Xavier et al. "Role of AMP-activated protein kinase in glucose-stimulated insulin secretion and preproinsulin gene expression". Journal of Biochemistry 371:761-774, 2003.

* cited by examiner

*Primary Examiner*—Robert C. Hayes
*Assistant Examiner*—Daniel E. Kolker
(74) *Attorney, Agent, or Firm*—Fish & Richardson P.C.

(57) ABSTRACT

A method of identifying a 5'AMP-activated protein kinase inhibitor for treating a neurodegenerative disease. Disclosed are a method and a packaged product for treating a neurodegenerative disease. Also disclosed is a method for treating a 5'AMP-activated protein kinase-related disease and a related packaged product.

7 Claims, No Drawings

SEQUENCE LISTING

```
<160> NUMBER OF SEQ ID NOS: 14

<210> SEQ ID NO 1
<211> LENGTH: 30
<212> TYPE: DNA
<213> ORGANISM: Artificial Sequence
<220> FEATURE:
<223> OTHER INFORMATION: Primer

<400> SEQUENCE: 1
atgaaggcct tcgagtccct caagtccttc                                         30

<210> SEQ ID NO 2
<211> LENGTH: 26
<212> TYPE: DNA
<213> ORGANISM: Artificial Sequence
<220> FEATURE:
<223> OTHER INFORMATION: Primer

<400> SEQUENCE: 2
ctcacggtcg gtgcagcggc tcctca                                             26

<210> SEQ ID NO 3
<211> LENGTH: 22
<212> TYPE: DNA
<213> ORGANISM: Artificial Sequence
<220> FEATURE:
<223> OTHER INFORMATION: Primer

<400> SEQUENCE: 3
cagtgtgtgg gttggagata ag                                                 22
```

<210> SEQ ID NO 4
<211> LENGTH: 23
<212> TYPE: DNA
<213> ORGANISM: Artificial Sequence
<220> FEATURE:
<223> OTHER INFORMATION: Primer

<400> SEQUENCE: 4
tgcagtatga gttccagtgt ttg                                    23

<210> SEQ ID NO 5
<211> LENGTH: 21
<212> TYPE: DNA
<213> ORGANISM: Artificial Sequence
<220> FEATURE:
<223> OTHER INFORMATION: Primer

<400> SEQUENCE: 5
actgatcgct ggagtgagat g                                      21

<210> SEQ ID NO 6
<211> LENGTH: 22
<212> TYPE: DNA
<213> ORGANISM: Artificial Sequence
<220> FEATURE:
<223> OTHER INFORMATION: Primer

<400> SEQUENCE: 6
gcagaaactt ggagcgtaag ag                                     22

<210> SEQ ID NO 7
<211> LENGTH: 24
<212> TYPE: DNA
<213> ORGANISM: Artificial Sequence
<220> FEATURE:
<223> OTHER INFORMATION: Primer

<400> SEQUENCE: 7
gattatcctg accagtttga tgac                                   24

<210> SEQ ID NO 8
<211> LENGTH: 23
<212> TYPE: DNA
<213> ORGANISM: Artificial Sequence
<220> FEATURE:
<223> OTHER INFORMATION: Primer

<400> SEQUENCE: 8
aagatcagtt cctccttggt ttc                                    23

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
ggcttcacag gagacatcag                                        20

<210> SEQ ID NO 10
<211> LENGTH: 22
<212> TYPE: DNA
<213> ORGANISM: Artificial Sequence
<220> FEATURE:
<223> OTHER INFORMATION: Primer -continued

```
<400> SEQUENCE: 10
cagaaccaga acgaacagaa ac                                             22

<210> SEQ ID NO 11
<211> LENGTH: 22
<212> TYPE: DNA
<213> ORGANISM: Artificial Sequence
<220> FEATURE:
<223> OTHER INFORMATION: Primer

<400> SEQUENCE: 11
caagcagaag agagaggagt tg                                             22

<210> SEQ ID NO 12
<211> LENGTH: 24
<212> TYPE: DNA
<213> ORGANISM: Artificial Sequence
<220> FEATURE:
<223> OTHER INFORMATION: Primer

<400> SEQUENCE: 12
cttagcagac attggaagaa acag                                           24

<210> SEQ ID NO 13
<211> LENGTH: 22
<212> TYPE: DNA
<213> ORGANISM: Artificial Sequence
<220> FEATURE:
<223> OTHER INFORMATION: Primer

<400> SEQUENCE: 13
tgacatcaag aaggtggtga ag                                             22

<210> SEQ ID NO 14
<211> LENGTH: 22
<212> TYPE: DNA
<213> ORGANISM: Artificial Sequence
<220> FEATURE:
<223> OTHER INFORMATION: Primer

<400> SEQUENCE: 14
agagtgggag ttgctgttga ag                                             22
```

HUNTINGTON'S DISEASE TREATMENT

BACKGROUND

Neurodegenerative diseases are disorders characterized by gradual and progressive loss of nerve cells. Examples of these diseases include Alzheimer's disease, Parkinson's disease, and Huntington's disease. Among them, Huntington's disease (HD) is an autosomal dominant disorder caused by a CAG trinucleotide expansion in exon 1 of the Huntingtin (Htt) gene. See, e.g., Perutz et al., Trends Biochem. Sci. 1999;24:58–63; and Rubinsztein et al., J. Med. Genet. 1999;36:265–270. HD patients have abnormal body movement, dementia, and psychiatric problems. Medications, such as dopamine blockers, reduce the abnormal movement and behavior, but do not stop the regression. Thus, there is a need for a new drug that effectively treats HD and other neurodegenerative diseases.

SUMMARY

This invention relates to use of 5'AMP-activated protein kinase inhibitor in treating a neurodegenerative disease.

In one aspect, the invention features a method of identifying a compound for treating a neurodegenerative disease, such as Huntington's disease. The method includes contacting a first cell expressing a 5'AMP-activated protein kinase (AMPK) with a compound, and determining an expression level, a phosphorylation level, or a kinase activity of the 5'AMP-activated protein kinase. The compound is determined to be effective in treating the neurodegenerative disease if the expression level, the phosphorylation level, or the kinase activity is lower than that determined in the same manner from a second cell except that the second cell is not contacted with the compound. Examples of the first and second cells include a glial cell and a neuronal cell. The method can be practiced both in vitro and in vivo. In an embodiment for an in vivo method, the first cell or the second cell is in a non-human animal, e.g., in the striatum of the non-human animal. A suitable non-human animal is a mouse, such as an R6/2 mouse.

A 5'AMP-activated protein kinase described above refers to a full-length 5'AMP-activated protein kinase polypeptide (e.g., the mammalian, yeast, or plant AMP-activated protein kinase described in Carling et al., 1994, J. Biol. Chem. 269:11442–11448) or its functional equivalent. A functional equivalent refers to a polypeptide derived from the 5'AMP-activated protein kinase protein, e.g., a fusion polypeptide or a polypeptide having one or more point mutations, insertions, deletions, truncations, or combination thereof. This polypeptide retains substantially the kinase activity of the 5'AMP-activated protein kinase, i.e., the ability to phosphorylate target proteins, such as those described in Lee et al., J. Biol. Chem. 2003; 278:39653–39661; Hong et al., J. Biol. Chem. 2003; 278:27495–27501; and Fryer et al., J. Biol. Chem. 2002; 277:25226–25232.

In another aspect, the invention features a method of treating a neurodegenerative disease, e.g., Huntington's disease. The method includes identifying a subject suffering from or being at risk for developing a neurodegenerative disease, and administering to the subject an effective amount of an inhibitor of 5'AMP-activated protein kinase. An "inhibitor" refers to a compound that represses the level of the gene expression, posttranslational modification (e.g., phosphrylation), or kinase activity of a 5'AMP-activated protein kinase in statistically significant manner. Examples of such agent include a small inorganic molecule, a small organic molecule, a peptide, an antibody, and a nucleic acid (e.g., an antisense RNA, a ribozyme, or an RNA interference agent). A small inorganic molecule example is CGS21680 as described in the Detailed Description and Examples sections below.

In a further aspect, the invention features a method of treating a 5'AMP-activated protein kinase-related disease. The method includes identifying a subject suffering from or being at risk for developing a 5'AMP-activated protein kinase-related disease, and administering to the subject an effective amount of the just-mentioned CGS21680. A 5'AMP-activated protein kinase-related disease refers to a disorder that is associated with an elevated level of the gene expression, phosphorylation, or kinase activity of 5'AMP-activated protein kinase. Examples of such a disease include diabetes and obesity.

Also within the scope of the invention are two packaged products. One packaged product includes a container, an effective amount of an inhibitor of 5'AMP-activated protein kinase, and a legend associated with the container and indicating administration of the an inhibitor of 5'AMP-activated protein kinase for treating a subject suffering from or being at risk for developing a neurodegenerative disease. The other packaged product includes a container, an effective amount of CGS21680, and a legend associated with the container and indicating administration of CGS21680 for treating a subject suffering from or being at risk for developing a 5'AMP-activated protein kinase-related disease.

The details of one or more embodiments of the invention are set forth in the accompanying description below. Other features, objects, and advantages of the invention will be apparent from the detailed description, and from the claims.

DETAILED DESCRIPTION

The present invention is based on an unexpected discovery that an AMPK inhibitor, e.g., CGS21680, effectively improved several major pathological characteristics of HD in an R6/2mouse model. Such an AMPK inhibitor can be used in treating HD and other neurodegenerative diseases.

Accordingly, the invention features a method for identifying an AMPK inhibitor for treating a neurodegenerative disease. An AMPK inhibitor can be obtained from commercial suppliers or identified according to the methods described below or any other methods well known in the art.

Candidate compounds (e.g., proteins, peptides, peptidomimetics, peptoids, antibodies, small molecules, or other drugs) can be obtained using any of the numerous approaches in combinatorial library methods known in the art. Such libraries include: peptide libraries, peptoid libraries (libraries of molecules having the functionalities of peptides, but with a novel, non-peptide backbone that is resistant to enzymatic degradation); spatially addressable parallel solid phase or solution phase libraries; synthetic libraries obtained by deconvolution or affinity chromatography selection; and the "one-bead one-compound" libraries. See, e.g., Zuckermann et al. 1994, J. Med. Chem. 37:2678–2685; and Lam, 1997, Anticancer Drug Des. 12:145. Examples of methods for the synthesis of molecular libraries can be found in, e.g., DeWitt et al., 1993, PNAS USA 90:6909; Erb et al., 1994, PNAS USA 91:11422; Zuckermann et al., 1994, J. Med. Chem. 37:2678; Cho et al., 1993, Science 261:1303; Carrell et al., 1994, Angew. Chem. Int. Ed. Engl. 33:2059; Carell et al., 1994, Angew. Chem. Int. Ed. Engl. 33:2061; and Gallop et al., 1994 J. Med. Chem. 37:1233. Libraries of compounds may be presented in solution (e.g., Houghten, 1992, Biotechniques 13:412–421), or on beads (Lam, 1991, Nature 354:82–84), chips (Fodor, 1993, Nature 364:555–556), bacteria (U.S. Pat. No. 5,223,409), spores (U.S. Pat. No. 5,223, 409), plasmids (Cull et al., 1992, PNAS USA 89:1865–1869), orphages (Scott and Smith 1990, Science 249:386–390; Devlin, 1990, Science 249:404–406; Cwirla et al., 1990, PNAS USA 87:6378–6382; Felici 1991, J. Mol. Biol. 222:301–310; and U.S. Pat. No. 5,223,409).

To identify an AMPK inhibitor, one can contact a candidate compound with a system containing an AMPK. The system can be a cell-free system or a cell-containing system, e.g., an in vitro cell line model or an in vivo animal model. In a cell-containing system, cells can naturally express the AMPK gene, or can be modified to express a recombinant nucleic acid. The recombinant nucleic acid can contain the AMPK gene coding region fused to a heterologous promoter or an AMPK gene promoter sequence fused to a reporter gene. One then measures the expression level, the phosphorylation level, or the kinase activity of the AMPK.

The expression level can be determined at either the mRNA level or at the protein level. Methods of measuring mRNA levels in a tissue sample or a body fluid are well known in the art. To measure mRNA levels, cells can be lysed and the levels of mRNA in the lysates or in RNA purified or semi-purified from the lysates can be determined by, e.g., hybridization assays (using detectably labeled gene-specific DNA or RNA probes) and quantitative or semi-quantitative RT-PCR (using appropriate gene-specific primers). Alternatively, quantitative or semi-quantitative in situ hybridization assays can be carried out using tissue sections or unlysed cell suspensions, and detectably (e.g., fluorescent or enzyme) labeled DNA or RNA probes. Additional mRNA-quantifying methods include RNA protection assay (RPA) and SAGE.

Methods of measuring protein levels in a tissue sample or a body fluid are also known in the art. Many such methods employ antibodies (e.g., monoclonal or polyclonal antibodies) that bind specifically to a target protein. In such assays, the antibody itself or a secondary antibody that binds to it can be detectably labeled. Alternatively, the antibody can be conjugated with biotin, and detectably labeled avidin (a polypeptide that binds to biotin) can be used to detect the presence of the biotinylated antibody. Combinations of these approaches (including "multi-layer sandwich" assays) can be used to enhance the sensitivity of the methodologies. Some of these protein-measuring assays (e.g., ELISA or Western blot) can be applied to body fluids or to lysates of cells, and others (e.g., immunohistological methods or fluorescence flow cytometry) applied to histological sections or unlysed cell suspensions. Methods of measuring the amount of label depend on the nature of the label and are well known in the art. Appropriate labels include radionuclides (e.g., $^{125}I$, $^{131}I$, $^{35}S$, $^{3}H$, or $^{32}P$), enzymes (e.g., alkaline phosphatase, horseradish peroxidase, luciferase, or β-glactosidase), fluorescent moieties or proteins (e.g., fluorescein, rhodamine, phycoerythrin, GFP, or BFP), or luminescent moieties (e.g., Qdot™ nanoparticles supplied by the Quantum Dot Corporation, Palo Alto, Calif.). Other applicable assays include quantitative immunoprecipitation or complement fixation assays.

The phosphorylation level and kinase activity of an AMPK can be measured by the methods described below in the Example section or by methods known in the art, e.g., those described in Rutter et al., 2003, Biochem. J.; 375:1–16; Lee et al., J. Biol. Chem. 2003; 278:39653–39661; Hong et al., J. Biol. Chem. 2003; 278:27495–27501; and Fryer et al., J. Biol. Chem. 2002; 277:25226–25232.

To determine the ability of a candidate compound to inhibit AMPK, one compares the level or activity obtained in the manner described above with a control level or activity obtained in the absence of the candidate compound. If the level or activity is lower than the control, the compound is identified as being effective for treating a neurodegenerative disease.

One can further verify the efficacy of a compound thus-identified using an animal model. For example, to verify a compound for treating HD, one can take advantage of the transgenic R6/2 mouse model (Mangiarini et al., 1996, Cell; 87:493–506). R6/2 mice express exon 1 of the human Huntingtin (Htt) gene with 122 or more CAG repeats. They progressively exhibit neurological phenotypes characteristic of HD, including choreiform-like movements, involuntary stereotypic movements, tremor, and epileptic seizures, as well as nonmovement disorder components. One can administer the compound to the mice and exam them according to the method describe below in the Example section or other standard techniques. Any statistically significant improvement of the neurological conditions of R6/2 mice indicates the compound is a candidate for treating HD.

The invention also features a method for treating a neurodegenerative disease. A subject to be treated can be identified by standard diagnosing techniques for a neurodegenerative disease, such as HD. Optionally, the subject can then be examined for the gene expression or kinase activity level of the AMPK polypeptide by methods described above. If the gene expression or kinase activity level is higher in a sample from the subject than that in a sample from a normal person, the subject is a candidate for treatment with an effective amount of an AMPK inhibitor.

"Treating" refers to administration of a compound to a subject, who has a neurodegenerative disease, with the purpose to cure, alleviate, relieve, remedy, prevent, or ameliorate the disorder, the symptom of the disorder, the disease state secondary to the disorder, or the predisposition toward the disorder. An "effective amount" refers to an amount of the compound that is capable of producing a medically desirable result, e.g., as described above, in a treated subject. The treatment method can be performed in vivo or ex vivo, alone or in conjunction with other drugs or therapy.

In an in vivo approach, an AMPK inhibitor is administered to a subject. Generally, the compound is suspended in a pharmaceutically-acceptable carrier (e.g., physiological saline) and administered orally or by intravenous infusion, or injected or implanted subcutaneously, intramuscularly, intrathecally, intraperitoneally, intrarectally, intravaginally, intranasally, intragastrically, intratracheally, or intrapulmonarily. For treatment of a neurodegenerative disease, such as HD, the compound can be delivered directly to the striatum, i.e., through intrastriatal injection.

The dosage required depends on the choice of the route of administration; the nature of the formulation; the nature of the patient's illness; the subject's size, weight, surface area, age, and sex; other drugs being administered; and the judgment of the attending physician. Suitable dosages are in the range of 0.01–100 mg/kg. Variations in the needed dosage are to be expected in view of the variety of compounds available and the different efficiencies of various routes of administration. For example, oral administration would be expected to require higher dosages than administration by i.v. injection. Variations in these dosage levels can be adjusted using standard empirical routines for optimization as is well understood in the art. Encapsulation of the compound in a suitable delivery vehicle (e.g., polymeric microparticles or implantable devices) may increase the efficiency of delivery, particularly for oral delivery.

Alternatively, a polynucleotide containing a nucleic acid sequence encoding an inhibitor of an AMPK can be delivered to a subject. The nucleic acid sequence can encode an anti-AMPK antibody, an anti-sense RNA, or a small interference RNA that targets the AMPK and inhibits its expression or kinase activity. The polynucleotide can be delivered by the use of polymeric, biodegradable microparticle or microcapsule delivery devices known in the art. Another way to achieve uptake of the nucleic acid is using liposomes, prepared by standard methods. The polynucleotide can be incorporated alone into these delivery vehicles or co-incorporated with tissue-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells (Cristiano, et al., 1995, J. Mol. Med. 73:479). Alternatively, tissue specific targeting can be achieved by the use of tissue-specific transcriptional regulatory elements that are known in the art. Delivery of "naked DNA" (i.e., without a delivery vehicle) to an intramuscular, intradermal, or subcutaneous site is another means to achieve in vivo expression.

In the above-mentioned polynucleotides, e.g., expression vectors, the nucleic acid sequence encoding an inhibitor of the AMPK is operatively linked to a promoter or enhancer-promoter combination. Suitable expression vectors include plasmids and viral vectors such as herpes viruses, retroviruses, vaccinia viruses, attenuated vaccinia viruses, canary pox viruses, adenoviruses and adeno-associated viruses.

As is well known in the art, the dosage for a patient depends upon various factors as described above. Dosages will vary, but a preferred dosage for administration of polynucleotide is about $10^6$ to $10^{12}$ copies of the polynucleotide molecule. This dose can be repeatedly administered as needed. Routes of administration can be any of those listed above.

In an ex vivo strategy, treating a subject with a neurodegenerative disease involves transfecting or transducing cells obtained from the subject with a polynucleotide encoding an AMPK inhibitor. Cells can be transfected in vitro with a vector designed to insert, by homologous recombination, a new, active promoter upstream of the transcription start site of a naturally occurring endogenous AMPK inhibitor gene in the cells' genome. After selection and expansion of cell that express the AMPK inhibitor at a desired level, the transfected or transduced cells are then returned to the subject. Examples of the cells include neural cells, hemopoietic cells (e.g., bone marrow cells, macrophages, monocytes, dendritic cells, T cells, or B cells), fibroblasts, epithelial cells, endothelial cells, keratinocytes, or muscle cells. Such cells act as a source of the AMPK inhibitor for as long as they survive in the subject.

The just-described ex vivo method includes the steps of harvesting cells from a subject, culturing the cells, transducing them with an expression vector, and maintaining the cells under conditions suitable for expression of an AMPK inhibitor. The transduction step is accomplished by any standard means used for ex vivo gene therapy, including calcium phosphate, lipofection, electroporation, viral infection, and biolistic gene transfer. Alternatively, liposomes or polymeric microparticles can be used. Cells that have been successfully transduced can then be selected, for example, for expression of the AMPK inhibitor. The cells may then be injected or implanted into the subject.

Also within the scope of the invention is a packaged product including a container, an effective amount of an AMPK inhibitor and a legend associated with the container and indicating administration of the inhibitor for treating a subject suffering from or being at risk for developing a neurodegenerative disease. The inhibitor can be admixed with a pharmaceutically acceptable carrier, including a solvent, a dispersion medium, a coating, an antibacterial and antifungal agent, and an isotonic and absorption-delaying agent.

The inhibitor can be formulated into dosage forms for different administration routes utilizing conventional methods. For example, it can be formulated in a capsule, a gel seal, or a tablet for oral administration. Capsules can contain any standard pharmaceutically acceptable materials such as gelatin or cellulose. Tablets can be formulated in accordance with conventional procedures by compressing mixtures of the inhibitor with a solid carrier and a lubricant. Examples of solid carriers include starch and sugar bentonite. The inhibitor can also be administered in a form of a hard shell tablet or a capsule containing a binder, e.g., lactose or mannitol, a conventional filler, and a tableting agent. The inhibitor can be administered via the parenteral route. Examples of parenteral dosage forms include aqueous solutions, isotonic saline or 5% glucose of the active agent, or other well-known pharmaceutically acceptable excipient. Cyclodextrins, or other solubilizing agents well known to those familiar with the art, can be utilized as pharmaceutical excipients for delivery of the therapeutic agent. Further, the inhibitor can be injected directly to the striatum via brain operation.

The efficacy of the inhibitor can be evaluated both in vitro and in vivo. For example, the inhibitor can be tested for its ability to repress gene expression or kinase activity of the AMPK in vitro. For in vivo studies, the inhibitor can be injected into an animal (e.g., an animal model) and its effects on a neurodegenerative disease are then accessed. Based on the results, an appropriate dosage range and administration route can be determined.

The above-described AMPK inhibitor, e.g., CGS21680, can also be used in treating other diseases (e.g., diabetes and obesity) that are associated with abnormally high level of AMPK gene expression or kinase activity. A subject to be treated can be identified by methods known in the art or by determining the gene expression or kinase activity level of the AMPK polypeptide in a sample prepared from a subject as described above. If the gene expression or kinase activity level of the AMPK polypeptide is higher in the sample from the subject than that in a sample from a normal person, the subject is a candidate for treatment with an effective amount of an AMPK inhibitor.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications recited herein are hereby incorporated by reference in their entirety.

EXAMPLE 1

The effects of CGS21680 on AMPK were studied using R6/2 transgenic mice. Male R6/2 mice and wild type littermates were obtained from Jackson Laboratories (Bar Harbor, Me., USA) and were mated with female control mice (B6CBAFI/J). Each offspring was genotyped by PCR using genomic DNA extracted from the tail to ensure that the number of CAG repeats remained approximately 150. Primers used were 5'-ATGAAGGCCTTCGAGTCCCT-CAAGTCCTTC-3' (SEQ ID NO:1) and 5'-CTCACG-GTCGGTGCAGCGGCTCCTCAGC-3' (SEQ ID NO:2). All animal experiments were performed under protocols approved by the Academia Sinica Institutional Animal Care and Utilization Conunittee, Taiwan.

CGS21680 (Research Biochemicals, Natick, Mass.) was dissolved in saline containing 1% DMSO and administered to the mice. More specifically, sixteen 7-week old R6/2 mice were divided into two groups (8 in each group) and were intraperitoneally injected with CGS21680 (5 µg/g body weight) and the same amount of the vehicle solvent once a day for up to 3.5 weeks.

Then, the striatal cytosolic fraction was collected from each mouse and subjected to Western blot analysis using the standard techniques as described in Rutter et al., Biochem. J. 2003;375:1–16. More specifically, membrane fractions were combined with a 2× sample buffer containing 125 mM Tris-HCl (pH 6.8), 20% glycerol, 1% SDS, 15% 2-mercaptoethanol, 200 mM dithiothreitol, and 0.01% bromphenol blue; boiled for 5 minutes; centrifuged to remove the insoluble material; and then separated on 8% separating gels. Following the electrophoresis, the proteins were transferred to a polyvinylidene difluoride membrane, blocked with 5% skim milk-phosphate buffered saline (PBS), and incubated with an anti-AMPK antiserum (1:1000 Abcam Limited, Cambridge, UK) or an anti-AMPKP antiserum (1:1000, Cell Signaling Technology, Beverly, Mass., USA) at 4° C. overnight. After three 5-minute washes in PBS, the membrane was incubated with peroxidase-conjugated donkey anti-rabbit IgG (1:5000, Amersham, UK) for 1 hour at room temperature and washed three times with PBS. Immuno-reactive bands were visualized by a light emitting nonradioactive method (ECL, Amersham, UK). The phosphorylation of AMPK at Thr172 was quantified by densitometry of the anti-AMPK-P immunoreactive bands using ImageQuant v.3.15 (Molecular Dynamics). The same experiment was conducted on wild type littermates, except that they had not been administrated with CGS21680.

It was found that all three group mice had about the same AMPK protein level. However, AMPK protein in the R6/2 mice treated with the vehicle had a much higher phosphorylation level (by more than 100%) than that in the control mice, indicating that a high AMPK protein phosphorylation level is associated with HD phenotypes. Unexpectedly, the CGS21680 administration significantly reduced the AMPK phosphorylation level in R6/2 mice by about 35%. Since AMPK phosphorylation level reflects its degree of activation, the results suggest that CGS21680 represses the kinase activity of AMPK.

EXAMPLE 2

R6/2 mice show impaired locomotor activities, including choreiform-like movements, involuntary stereotypic movements, tremor, and epileptic seizures. The effects of CGS21680 on these locomotor activities of R6/2 mice were studied.

Two groups of R6/2 mice (8 per group) were administered with CGS21680 and the vehicle solvent for up to 5 weeks in the same manner described above in Example 1. Twenty-four hours after each administration, the locomotor activity of each mouse was measured for 10 minutes according to the method described in Lee et al., Chin. J. Physiol. 1992;35: 317–336. Briefly, each mouse was placed in an activity monitor (Coulbourn Instruments, Allentown, Pa., USA) equipped with 16×16 horizontal sensors, which were used to monitor the mouse's floor position. The locomotor activity was measured by the total number of beam breaks in an X-Y plane recorded every 10 minutes.

It was found that, at week 2 after the administration, mice received the vehicle exhibited typical locomotor activity deterioration. In contrast, those administered with CGS21680 did not exhibit such deterioration, but showed improvement in the locomotor activity. The difference between the two groups was statistically significant (according to Student's t-test). This result suggests that the CGS 21680 administration improves the locomotor activities of R6/2 mice.

The motor coordination of each mouse was also examined by rotarod performance using standard techniques. No difference was found. It is known that the motor coordination of an R6/2 mouse starts to deteriorate at the age of 4 weeks, which is 3 weeks prior to the time of the CGS 21680 treatment. It is expected that CGS 21680 administration prior to 4 week of age might improve the motor coordination of an R6/2 mouse.

EXAMPLE 3

Effect of CGS21680 on neurochemistry were examined in R6/2 mice. It is known that HD patients have changes in neurochemicals, such as choline-containing compounds and N-acetylaspartate (NAA). An increase in choline-containing compounds and a decrease in NAA are associated with neural traumas and axonal dysfunction or loss. See, e.g., Waters et al., Biochem. Pharmacol. 2002;64:67–77; and Jenkins et al., J Neurochem. 2000;74:2108–2119. Thus, the choline containing compound and NAA levels in R6/2 mice were examined using standard techniques.

Two groups of R6/2 mice (6 in each group) were administered with CGS21680 and the vehicle in the manner described above. A group of 6 wild type littermates were also administered with the vehicle. At week 2 after the administration, the mice were analyzed for neurochemical changes by in vivo proton localized magnetic resonance spectroscopy ($^1$H-MRS).

More specifically, the mice were anesthetized by intraperitoneal injection of chloral hydrate (4.088 mg/10 g body weight). MRS was performed on a Biospec 4.7 T spectrometer with an active shielding gradient at 6.9 G/cm in 500 µs. Each mouse was placed in a prone position with a custom-designed head-holder. A 20-cm birdcage coil was used for RF excitation, and a 2-cm-diameter surface coil placed directly over the head was used for signal reception. The volume of interest (VOI) for $^1$H-MRS measurements over the striatum was selected on the basis of a coronal diffusion-weighted image using a pulse gradient spin-echo diffusion method with a repetition time (TR) of 1500 ms, an echo time (TE) of 62 ms, a field of view of 3×3 cm, a slice thickness of 1 mm, a b value of 1300 s/mm$^2$, number averages of 2, and a 256×128 matrix size zero filled to 256×156. The diffusion-sensitive gradients were applied in the read (x) direction before and after the refocusing pulse. The point-resolved spectroscopy (PRESS) sequence, preceded by three consecutive chemical shift selective saturation (CHESS) pulses for water suppression, was used for localized spectroscopy with a 3.5×3.5×3.5 mm$^3$ voxel located in the striatum region, a spectral width of 4000 Hz, a TR of 3.5 s, a TE of 136 ms, signal averages of 256, and a total scanning time of 8 min 32 s. The peak areas of NAA, choline, and creatine were recognized. The ratios of striatum NAA and choline relative to creatine were used for statistical analysis.

It was found that the average choline/creatine ratio of the vehicle-administered R6/2 mice was much higher than that of the wild type mice (1.74±0.12 vs. 1.25±0.05). In contrast, the CGS21680 administration reversed the elevated choline/creatine ratio in R6/2 mice (1.74±0.12 and 1.44±0.08, respectively, p=0.023). As changes in choline-containing compound levels affect the composition of plasma membranes, they may alter the electro-physiological activity of the plasma membranes and related signal transduction (Gopalakrishna et al., J. Cell. Biochem. 2000;77:517–528 and Shander et al., J. Mol. Cell. Cardiol. 1996;28:743–753.). Indeed, R6/2 mice exhibit significant changes in various electrophysiological properties (Klapstein et al., J Neurophysiol. 2001;86:2667–2677). Thus, the above results suggest that the CGS21680 treatment reverses pathological progression of R6/2 mice by reducing the choline level to a level similar to that of wild type mice.

NAA levels were also examined in the mice by $^1$H-MRS. It was found that the average NAA/creatine ratio of the R6/2 mice administered with the vehicle was much lower than that of the wild type mice (0.67±0.02 vs. 1.12±0.04), indicating significant neuronal damage in the R6/2 mice. However, the CGS 21680 treatment did not affect the NAA/creatine ratio in R6/2 mice (0.67±0.02 and 0.69±0.02 for none-treated and treated mice, respectively, p=0.691). As NAA levels are reduced in R6/2 mice when they are 4 weeks old, the CGS 21680 treatment starting at the age of 7 weeks is not able to reverse the neuronal damage and the associated decrease in NAA levels. It is expected that administration of CGS 21680 at an earlier age (e.g., 4 weeks old) might increase the NAA levels.

EXAMPLE 4

Effects of CGS21680 on striatal atrophy were studied. Striatal atrophy is one of the major characteristics of HD. In R6/2 mice, marked progressive atrophy of the striatum was found at the age of 3 to 13 weeks (Ferrante et al., J. Neurosci. 2000;20:4389–4397). Thus, the above-described CGS 21680-treated and vehicle-treated R6/2 mice were examined for striatal atrophy.

Each of the mice was anesthetized using sodium pentobarbital (100 μg/g), and intracardially perfused with 4% paraformaldehyde in 0.1 M phosphate buffer (PB, pH 7.4). The brain was carefully removed, post-fixed with 4% paraformaldehyde/0.1 M PB for 2–5 hours, and immersed in 30% glycerol in 0.1 M PB. Then, it was cut at 20 μm on a freezing microtome (CM3050, Leica Microsystems Nussloch, Nussloch, Germany). Serial-cut coronal tissue sections from the rostral segment of the neostriatum to the level of the anterior commissure (interaural 5.34 mm/bregma 1.54 mm to interaural 3.7 mm/bregma −0.1 mm) were used to define atrophy of the striatum and enlargement of the lateral ventricles. Total areas of the striatum or the lateral ventricles were measured using the software NIH Image 1.62. Nissl-stained sections were quantified by counting the corresponding types of cells in defined areas of photomicrographs taken using a phase contrast microscope.

It was found that the administration of CGS 21680 reduced the size of ventricular enlargement (1.63±0.14 and 0.91±0.14 mm$^2$, for vehicle- and CGS 21680-treated R6/2 mice, respectively, p<0.001, n=5) in the R6/2 mice at 12 weeks old. This result suggests that the administration of CGS 21680 reverses striatal atrophy in HD.

EXAMPLE 5

Neurotrophic factors, such as nerve growth factor (NGF), brain-derived growth factor (BDNF), glial cell line-derived neurotrophic factor (GDNF), and ciliary neurotrophic factor (CNTF), have been shown to exert neuronal protective effects. See e.g., Perez-Navarro et al., J. Neurochem. 2000; 75:2190–2199; Alberch et al., Brain Res. Bull. 2002;57: 817–822; and Mittoux et al., Neuroscience 2002;22:4478–4486. Thus, the effects of CGS21680 on neurotrophic factors were examined using the quantitative real-time RT-PCR technique.

Total RNA was purified from each of the above-described administrated mice and their littermates, and was treated with RNase-free DNase I (RQI, Promega, Madison, Wis., USA) following the manufacturer's protocol to remove genomic DNA. cDNA synthesis and quantitative real-time RT-PCR were performed using the TITANIUM One-Step RT-PCR kit (Clontech, Palo Alto, Calif., USA) containing SYBR Green I (BioWhittaker Molecular Applications; BMA, Rockland, Me., USA). More specifically, the first-strand cDNA was synthesized at 50° C. for 60 minutes and denatured at 95° C. for 10 minutes. PCR reactions were then carried out in the same tubes using the following conditions for 40 cycles: 95° C. for 30 seconds, 60° C. for 30 seconds, and 68° C. for 60 seconds. The sequences of forward and reverse primers ("F" and "R," respectively) are listed in Table 1 below:

TABLE 1

Gene-specific primers used for real-time RT-PCR assays

| Gene | GenBank Accession no. | Primer pairs | Amplicon size (bp) |
| --- | --- | --- | --- |
| NGF | V00836 | F: 5'-CAGTGTGTGGGTTGGAGATAAG-3' (SEQ ID NO:3) R: 5'-TGCAGTATGAGTTCCAGTGTTTG-3' (SEQ ID NO:4) | 188 |
| CNTF | U05342 | F: 5'-ACTGATCGCTGGAGTGAGATG-3' (SEQ ID NO:5) R: 5'-GCAGAAACTTGGAGCGTAAGAG-3' (SEQ ID NO:6) | 173 |

TABLE 1-continued

Gene-specific primers used for real-time RT-PCR assays

| Gene | GenBank Accession no. | Primer pairs | Amplicon size (bp) |
|---|---|---|---|
| GDNF | D88264 | F: 5'-GATTATCCTGACCAGTTTGATGAC-3' (SEQ ID NO:7)<br>R: 5'-AAGATCAGTTCCTCCTTGGTTTC-3' (SEQ ID NO:8) | 260 |
| BDNF | NM_007540 | F: 5'-GGCTTCACAGGAGACATCAG-3' (SEQ ID NO:9)<br>R: 5'-CAGAACCAGAACGAACAGAAAC-3' (SEQ ID NO:10) | 147 |
| BFGF | NM_008006 | F: 5'-CAAGCAGAAGAGAGGAGTTG-3' (SEQ ID NO:11)<br>R: 5'-CTTAGCAGACATTGGAAGAAACAG-3' (SEQ ID NO:12) | 270 |
| GAPDH | NM_008084 | F: 5'-TGACATCAAGAAGGTGGTGAAG-3' (SEQ ID NO:13)<br>R: 5'-AGAGTGGGAGTTGCTGTTGAAG-3' (SEQ ID NO:14) | 109 |

Independent RT-PCRs were performed using the same RNAs for each neurotrophic factor gene (target gene) and glyceraldehyde-3-phosphate dehydrogenase (GAPDH, reference gene). Real-time fluorescence monitoring and melting curve analysis were performed using Rotor-Gene 3000 (Corbett Research, Sydney, Australia). Negative controls (containing no DNA) were included in each experiment. A melting curve was created at the end of each PCR cycle to confirm that a single product was amplified. Data were analyzed by the Rotor-Gene 3000 operating software version 4.6.94 (Corbett Research) to determine the threshold cycle (CT) above the background for each reaction. The relative transcript amount of each target gene, calculated using standard curves of serial RNA dilutions, was normalized to that of GAPDH amplified from the same RNA.

It was found that the expressions of NGF, BDNF, and GDNF were markedly reduced in the striata of the R6/2 mice treated with the vehicle as compared with those of the wild type mice, indicating that these decreases might contribute to the severe degeneration of the striatum. In contrast, increased CNTF levels were found in the striata of the R6/2 mice as compared to those of the wild type mice. As CNTF is neuronalprotective upon progressive striatal degeneration, the elevated CNTF level in the striatum of a R6/2 mouse indicates an adaptive mechanism to protect against mutant Htt with expanded polyQ (Mittoux et al., Neuroscience 2002;22:4478–4486). No difference was found in the level of the basic fibroblast growth factor (bFGF) between wild type and R6/2 mice.

Finally, the CGS 21680 treatment did not change the striatum expression level of any of the trophic factors examined. This result suggests that CGS 21680 improves the conditions of an R6/2 mouse through a trophic-factor-independent manner.

EXAMPLE 6

Effects of CGS21680 on adenosine receptor were examined. Adenosine is an important factor that regulates various physiological functions via four distinct adenosine receptor subtypes ($A_1$, $A_{2A}$, $A_{2B}$, and $A_3$). Take the $A_{2A}$ adenosine receptor ($A_{2A}$-R) for an example, its stimulation delays apoptosis in human neutrophils, protects the hippocampus from excitotoxicity in a kainate model, and enhances cell viability during hypoxia. See, e.g., Walker et al., J. Immunol. 1997; 158:2926–2931; Jones et al., Neuroscience 1998;85: 229–237; and Kobayashi et al., J. Biol. Chem. 1999;274: 20358–65. In addition, $A_{2A}$-R stimulation rescues the blockage of NGF-induced neurite outgrowth when the NGF-evoked MAPK cascade is suppressed (Cheng et al., J. Biol. Chem. 2002;277:33930–33942.). In the central nervous system, the $A_{2A}$-R gene is highly expressed in GABAergic striopallidal neurons that selectively degenerate during progression of HD (Glass et al., Neuroscience 2000;97:505–519). During the progression of HD, the expression of striatal $A_{2A}$-R is markedly reduced probably due to loss of striatal GABAergic neurons (Sapp et al., Neuroscience 1995;64:397–404). Thus, the expression and function of striatal $A_{2A}$-R, such as to activate adenylyl cyclase (Lai et al., Mol. Pharmacol. 1999;56:644–650), were examined in the above-described R6/2 mice.

The protein level of $A_{2A}$-R was examined by Western Blot in the same manner described in Example 1 above. Primary antibodies used were anti-Gsα antibody (1:2000; DuPont New England Nuclear, Wilmington, Del., USA) and anti-AC5N (1:5000), which was raised against a recombinant protein containing amino acids 1 to 240 of type V adenylyl cyclase (ACV, a major striatal AC).

It was found that the average $A_{2A}$-R protein level in the striata of R6/2 mice was significantly lower than that of wild type mice. It was also found that the expression levels of ACV and the short form of the Gsα protein (GsαS) were significantly reduced in the R6/2 mice. This is consistent with the reduced forskolin-evoked adenylyl cyclase activity. In contrast, the expression of the long form Gsα protein (GsαL) was elevated in the striatum of R6/2 mice, indicating that mutant Htt with polyQ expansion differentially modulated the expression of different signaling molecules.

The activity of adenylyl cyclase was evaluated according to the method described in Chem et al., Mol. Pharmacol. 1995;48:1–8. Briefly, striatal tissues were isolated from the mice and sonicated in a lysis buffer (0.4 mM EDTA, 1 mM EGTA, 25 mM Tris-HCl, 250 mM sucrose, 0.1 mM leupeptin, and 40 μM PMSF, pH 7.4) using a W-380 sonicator (Ultrasonics, Farmingdale, N.Y., USA) at a setting of 20% output power for a total of 45 seconds. The resultant homogenate was centrifuged at 50,000×g for 30 minutes and the P1 membrane fractions and the soluble fractions were collected. The adenylyl cyclase activity assay was performed at 37° C. for 10 minutes in a 400-μl reaction mixture containing 1 mM ATP, 100 mM NaCl, 50 mM Hepes, 0.2 mM EGTA, 100 μM rolipram, 6 mM MgCl$_2$, 1 μM GTP, and 20 μg of membrane protein. The reactions were stopped by adding 0.6 ml of 10% TCA. The cAMP formed was isolated by Dowex chromatography (Sigma, St. Louis, Mo., USA) and was assayed to the method described in Chern et al. The enzymatic reaction was in a linear range for up to 30 minutes with up to 40 μg of membrane proteins.

Unexpectedly, it was found that, in the R6/2 mice, the adenylyl cyclase activities induced by CGS21680 were much higher level than those in the wild type mice. In contrast, the adenylyl cyclase activities induced by a general adenylyl cyclase activator forskolin (Sigma, St. Louis, Mo.) were much lower than those in the wild type mice. Further, the administration of CGS 21680 to the R6/2 mice for two weeks did not significantly affect protein expression levels or the activity of the A$_{2A}$-R, suggesting that chronic administration of CGS 21680 does not desensitize the A2A-R in R6/2 mice.

These results indicate that although the expression levels of the A$_{2A}$-R is reduced in R6/2 mice, stimulation of the A$_{2A}$-R effectively elevates cAMP contents to a level no less than that of wild type mice.

EXAMPLE 7

Hyperglycemia has been found in HD patients and R6/2 mice. Thus, effects of CGS21680 on hyperglycemia were examined in R6/2 mice. The above-described R6/2 mice and wild type littermates were decapitated and blood samples (1 to 1.5 ml) were collected from each mouse using standard techniques. Blood glucose levels were measured using ABBOTT Alcyon 300i (ABBOTT Labs, USA).

It was found that the blood glucose levels in the R6/2 mice not treated with CGS21680 were higher than those in the wild type mice by approximately 1-fold. In contrast, chronic CGS21680 treatment reduced the aberrantly elevated blood glucose level in R6/2 mice to a level comparable to that in the wild type mice. This result indicates that CGS21680 (1) improves glucose regulation and energy metabolism in R6/2 mice and (2) can be used in treating diabetes and obesity.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method of ameliorating the locomotor activity symptoms associated with Huntington's disease, the method comprising:
   identifying a subject suffering from or being at risk for developing Huntington's disease;
   administering to the subject an amount of CGS21680 effective in ameliorating the symptoms;
   determining the level of phosphorylation at residue Thr-172 or of catalytic activity of 5' AMP-activated protein kinase in a sample obtained from the subject after the administering step; and
   comparing the level of the phosphorylation or of the catalytic activity with a control level to confirm inhibition of the activity.

2. The method of claim 1, wherein CGS21680 is administered orally, intravenously, subcutaneously, intramuscularly, intrathecally, intraperitoneally, intrarectally, intravaginally, intranasally, intragastrically, intratracheally, intrapulmonarily, or intrastriataly.

3. The method of claim 1, wherein the subject is identified by a process including obtaining a sample from the subject and examining the phosphorylation level at residue Thr-172 or catalytic activity level of a 5' AMP-activated protein kinase, wherein the subject is identified to be a candidate for treatment with CGS21680 if the phosphorylation or catalytic activity level is higher than a normal level in a normal sample from a normal subject.

4. The method of claim 1, wherein CGS21680 is administered at 5 μg/g body weight once a day.

5. The method of claim 4, wherein CGS21680 is administered for up to 3.5 weeks.

6. The method of claim 1, wherein the control level is obtained from a normal subject.

7. The method of claim 1, wherein the control level is that of phosphorylation at residue Thr-172 or of catalytic activity of the 5' AMP-activated protein kinase in a control sample obtained from the subject before the administering step.

* * * * *